United States Patent
Yamaguchi et al.

(10) Patent No.: US 9,060,514 B2
(45) Date of Patent: Jun. 23, 2015

(54) EFFICACY-ENHANCING AGENT COMPOSITION FOR AGRICULTURAL CHEMICALS

(75) Inventors: Katsuhiko Yamaguchi, Wakayama (JP); Kazuhiko Kurita, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 13/701,315

(22) PCT Filed: Jul. 11, 2011

(86) PCT No.: PCT/JP2011/065752
§ 371 (c)(1),
(2), (4) Date: Dec. 12, 2012

(87) PCT Pub. No.: WO2012/008391
PCT Pub. Date: Jan. 19, 2012

(65) Prior Publication Data
US 2013/0090240 A1 Apr. 11, 2013

(30) Foreign Application Priority Data

Jul. 12, 2010 (JP) .................................. 2010-157659
Jul. 4, 2011 (JP) .................................. 2011-148059

(51) Int. Cl.
| | | |
|---|---|---|
| *A01N 25/02* | (2006.01) | |
| *A01N 45/02* | (2006.01) | |
| *A01N 25/30* | (2006.01) | |
| *A01N 31/02* | (2006.01) | |
| *A01N 33/12* | (2006.01) | |
| *A01N 43/08* | (2006.01) | |

(52) U.S. Cl.
CPC ................ *A01N 45/02* (2013.01); *A01N 25/02* (2013.01); *A01N 25/30* (2013.01); *A01N 31/02* (2013.01); *A01N 33/12* (2013.01); *A01N 43/08* (2013.01)

(58) Field of Classification Search
None
See application file for complete search history.

(56) References Cited

U.S. PATENT DOCUMENTS

| | | | | |
|---|---|---|---|---|
| 5,164,179 A | * | 11/1992 | Hioki et al. ................. | 424/78.08 |
| 5,863,909 A | | 1/1999 | Kurita et al. | |
| 2009/0203756 A1 | * | 8/2009 | Falk et al. .................... | 514/373 |

FOREIGN PATENT DOCUMENTS

| | | | |
|---|---|---|---|
| EP | 0 498 785 A1 | 8/1992 | |
| JP | 4-352704 A | 12/1992 | |
| JP | 5-221805 A | 8/1993 | |
| JP | 7-133205 A | 5/1995 | |
| JP | 8-151302 A | 6/1996 | |
| JP | 8-259404 A | 10/1996 | |
| JP | 3113161 B2 | 11/2000 | |
| JP | 2004-83540 A | 3/2004 | |
| JP | 2006-137728 A | 6/2006 | |
| JP | 2007-176855 A | 7/2007 | |
| JP | 2007-284437 A | 11/2007 | |
| JP | 2007-326832 A | 12/2007 | |
| JP | 2008-260741 A | 10/2008 | |
| JP | 2009-227664 A | 10/2009 | |
| WO | WO 2007033764 A2 | * | 3/2007 |

OTHER PUBLICATIONS

Human translation of JP 08-259404 A.*
International Preliminary Report on Patentability for International Patent Application No. PCT/JP2011/065752, dated Feb. 12, 2013.
Machine-generated translation for JP-2004-83540-A, published Mar. 18, 2004.
Machine-generated translation for JP-2006-137728-A, published Jun. 1, 2006.
Machine-generated translation for JP-176855-A, published Jul. 12, 2007.
Machine-generated translation for JP-2007-326832-A, published Dec. 20, 2007.
Machine-generated translation for JP-2008-260741-A, published Oct. 30, 2008.
Machine-generated translation for JP-2009-227654-A, published Oct. 8, 2009.
Machine-generated translation for JP-5-221805-A, published Aug. 31, 1993.
Machine-generated translation for JP-8-259404-A, published Oct. 8, 1996.
International Search Report issued in PCT/JP2011/065752 mailed Aug. 9, 2011.
The Office Action, dated Jan. 13, 2015, issued in the corresponding Japanese Patent Application No. 2011-148059.

* cited by examiner

*Primary Examiner* — Sue Liu
*Assistant Examiner* — Thor Nielsen
(74) *Attorney, Agent, or Firm* — Birch, Stewart, Kolasch & Birch, LLP

(57) ABSTRACT

The present invention provides the efficacy-enhancing agent composition for agricultural chemicals containing (A) the sorbitan fatty acid ester surfactant, (B) the rosin-oxyalkylene adduct surfactant or a specified quaternary ammonium salt surfactant, and (C) a specified glycol ether solvent.

10 Claims, No Drawings

EFFICACY-ENHANCING AGENT COMPOSITION FOR AGRICULTURAL CHEMICALS

FIELD OF THE INVENTION

The present invention relates to an efficacy-enhancing agent of agrichemical activity and an agrichemical composition.

BACKGROUND OF THE INVENTION

Agrichemicals including pesticides, bactericides, herbicides, miticides, and plant growth regulators are used in various preparation forms such as emulsion, wettable powder, granule, powder, and flowable concentrate. These preparations already have been designed to maximize the effects of an active ingredients of an agrichemical in various ways, and are hard to achieve a further improvement in agrichemical effectiveness by devising a method of preparing. Developing a new agrichemical is harder than devising. Therefore, it is industrially significant to enhance the activity of a known agricultural chemical. As thus, improvements of various agents used together with agrichemicals have conventionally been studied in various approaches.

JP-A08-151302 (corresponding to JP-B3113161) discloses an efficacy-enhancing agent composition for agricultural chemicals, containing a sorbitan fatty acid ester surfactant and a resin acid or quaternary ammonium salt surfactant. JP-A2007-284437 discloses a preservation-stabilized agricultural or epidemic-protective emulsion containing calcium alkylbenezenesulfonate but not a polyoxyalkylene alkyl phenyl ether surfactant or xylene, and describes use of a small amount of an alcohol to increase storage stability at low temperature. JP-A2004-83540 discloses an agricultural spreading agent containing a specified nonionic surfactant and an anion surfactant at a specified ratio to the nonionic surfactant.

SUMMARY OF THE INVENTION

The present invention relates to an efficacy-enhancing agent composition for agricultural chemicals, containing (A) a sorbitan fatty acid ester surfactant, (B) a rosin-oxyalkylene adduct surfactant or a quaternary ammonium salt surfactant represented by the formula (B1), and (C) a glycol ether solvent represented by the formula (C1), wherein the content of (A) is 20 to 60% by weight, the content of (B) is 0.2 to 6% by weight and the content of (C) is 30 to 70% by weight:

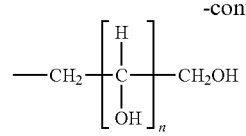
(B1)

wherein at least one of $R^1$, $R^2$ and $R^3$ is a linear or branched alkyl or alkenyl group, having 8 to 30 carbon atoms, the other is one of —$CH_3$, —$CH_2CH_3$,

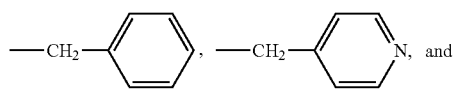, and

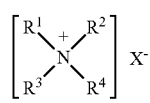

(wherein, n=1 to 5),
or combination thereof;
R4 represents —$CH_3$ or —$CH_2CH_3$; and
a counter ion $X^-$ represents one, two or more anionic groups derived from an anionic oligomer or polymer, having an average molecular weight of 300 to 20000, selected from the group consisting of the followings 1) to 3), 1) polymers containing one, two or more units derived from an essential construction monomer selected from the group consisting of unsaturated carboxylic acids and derivatives thereof,
2) polymers containing styrenesulfonic acid as an essential construction monomer,
3) formalin condensates of sulfonated polycyclic aromatic compounds that may be substituted with a hydrocarbon group, $$R^5—O—(CH_2CH_2O)_n—H \qquad (C1)$$

wherein, R5 represents a linear or branched alkyl group having 1 to 6 carbon atoms or a linear or branched alkenyl group having 2 to 6 carbon atoms; and n represents 2 or 3.

The present invention also relates to an agrichemical composition, containing the efficacy-enhancing agent composition for agricultural chemicals of the present invention and an active ingredient selected from effective ingredients in bactericides, pesticides, miticides, herbicides, and plant growth regulators, wherein a weight ratio of the total of (A) and (B) in the efficacy-enhancing agent composition to the active ingredient of an agrichemical, [(A)+(B)]/active ingredient of an agrichemical, is 0.03 to 50.

The present invention also relates to an agrichemical preparation, containing an individual package of the efficacy-enhancing agent composition for agricultural chemicals of the present invention and an individual package of an agrichemical composition containing an active ingredient selected from effective ingredients in bactericides, pesticides, miticides, herbicides, and plant growth regulators.

The present invention also relates to a method for cultivating a plant, including applying an agrichemical composition containing the efficacy-enhancing agent composition for agricultural chemicals of the present invention and an active ingredient selected from effective ingredients in bactericides, pesticides, miticides, herbicides, and plant growth regulators to a subject to the active ingredient of agrichemicals.

The present invention also relates to a method for enhancing an agrichemical, including applying an agrichemical composition, containing the efficacy-enhancing agent composition for agricultural chemicals of the present invention and an active ingredient selected from an effective ingredient in bactericides, pesticides, miticides, herbicides, and plant growth regulators, to a subject to the active ingredient of agrichemicals.

The present invention also relates to use of the efficacy-enhancing agent composition as an efficacy-enhancing agent of agrichemicals, and then use of the efficacy-enhancing agent composition as an efficacy-enhancing agent of agrichemicals in which the agrichemical is selected from active ingredients in bactericides, pesticides, miticides, herbicides, and plant growth regulators.

The present invention also relates to use of an agrichemical composition containing the efficacy-enhancing agent composition for agricultural chemicals of the present invention and an active ingredient selected from effective ingredients in bactericides, pesticides, miticides, herbicides, and plant growth regulators for production of an agricultural product.

DETAILED DESCRIPTION OF THE INVENTION

From the viewpoint of environmental protection, an amount of a surfactant used in preparing an efficacy-enhancing agent of agrichemical activity should be desirably reduced to as small an amount as possible. It, however, is difficult to prepare a liquid composition with such a reduced amount of the surfactant. In addition, uniform adhesion and stable fixation of an active ingredient of an agrichemical to an intended subject, for example, an agricultural product or weed may also be decreased. Therefore, there is a demand for developing an efficacy-enhancing agent composition for agricultural chemicals with a reduced amount of a surfactant and can enhance wetting property (uniformly adhering) and fixing of an agrichemical.

The present invention provides an efficacy-enhancing agent composition for agricultural chemicals that can be easily prepared and can enhance properties of wetting (uniformly adhering) and fixing of an agrichemical.

According to the present invention, provided is an efficacy-enhancing agent composition for agricultural chemicals that can be easily prepared, has a good stability at a low temperature, and can enhance properties of wetting (uniformly adhering) and fixing of an agrichemical on a subject, such as an agricultural product and a weed, to which an active ingredient of the agrichemical is applied. An easy preparation is advantageous to reduce a used amount of a surfactant.

[Efficacy-Enhancing Agent Composition for Agricultural Chemicals]

The efficacy-enhancing agent composition for agricultural chemicals of the present invention contains (A) the sorbitan fatty acid ester surfactant [hereinafter, referred to as component (A)], (B) the rosin-oxyalkylene adduct surfactant or the quaternary ammonium salt surfactant represented by the formula (B1) [hereinafter, referred to as component (B)], and (C) the glycol ether solvent represented by the formula (C1) [hereinafter, referred to as component (C)].

For the efficacy-enhancing agent composition for agricultural chemicals of the present invention, the reason of the easy preparation thereof is still unknown, but assumed that the component (C) has a similar FILE to components (A) and (B) and a similar structure to a surfactant, and accordingly has a good compatibility with components (A) and (B). The reason of improving wettability (uniform adhesion) and fixation of an agrichemical is also unknown, but assumed that the component (C) has surfactant-like properties, and accordingly promotes the effects of components (A) and (B).

<Component (A)>

Examples of the sorbitan fatty acid ester surfactant used in the present invention include sorbitan fatty acid esters and sorbitan fatty acid ester-alkylene oxide adducts. Particularly preferred are sorbitan fatty acid esters.

Any of mono-ester, di-ester and tri-ester of sorbitan fatty acid can be used. In general, a mixture of these esters is used. For improving fixation of an agrichemical and from the viewpoint of HLB, the mixture preferably has a monoester content of 40 to 70% by weight. For improving stability at low temperature and from the viewpoint of melting point of an ester, a fatty acid constructing the ester preferably has 8 to 22 carbon atoms. Specific examples of the fatty acid include capric acid, lauric acid, palmitic acid, oleic acid, stearic acid and the like.

A sorbitan fatty acid ester-alkylene oxide adduct is produced, for example, by adding an oxyalkylene compound to sorbitan and esterifying the adduct with a fatty acid. Examples of the oxyalkylene compound to add include ethylene oxide, propylene oxide, and butylene oxide. For improving dispersibility in water, particularly preferred is ethylene oxide. For improving fixation of an agrichemical and from the viewpoint of HLB, the alkylene oxide is added in an average mole number of 2 to 30 moles, and preferably 5 to 25 moles.

<Component (B)>

In the present invention, either a rosin-oxyalkylene adduct or a specific quaternary ammonium salt surfactant is used as the component (B) together with components (A) and (C). For improving fixation of an agrichemical and stability at low temperature, preferred is the rosin-oxyalkylene adduct.

The rosin-oxyalkylene adduct is produced by adding an alkylene oxide to a rosin. From the viewpoint of dispersibility in water, the rosin-oxyalkylene adduct is preferably produced by adding an alkylene oxide, preferably containing ethylene oxide, on the average in the amount of 2 to 50 moles, more preferably 5 to 40 moles, and even more preferably 8 to 30 moles.

In the invention, the "rosin" refers to a resin acid contained in a residue of a resin oil obtained from mainly pines by removing volatile substances such as essential oils, containing abietic acid and analogs thereof, and pimaric acid and the like in major proportions. The rosin is of natural origin, and has some varieties in composition and physical properties. In the present invention, any commercially available rosin can be used. For improving fixation of an agrichemical, among commercial rosins, commercial tall rosin is particularly preferred.

The quaternary ammonium salt used in the present invention is represented by the formula (B1), and includes various structures according to a kind of R1 to R4 and X$^-$. In the present invention, the quaternary ammonium salt can have any of such structures. From the viewpoints of adhesion and fixation of an agrichemical to a subject including pests, agricultural products, and weeds, the quaternary ammonium salt preferably has a structure of the formula (B1) in which at least one of R$^1$, R$^2$, and R$^3$ represents a linear or branched alkyl or alkenyl group having 8 to 30 carbon atoms, the other is one selected from —CH$_3$, —CH$_2$CH$_3$, and

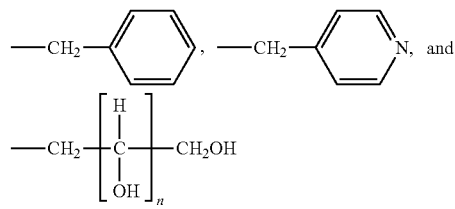

(wherein, n=1 to 5), or combination thereof;

R$^4$ represents —CH$_3$ or —CH$_2$CH$_3$; and a counter ion X$^-$ represents one, two or more anionic groups derived from an anionic oligomer or polymer having an average molecular weight of 300 to 20000, selected from the followings 1) to 3), 1) polymers containing at least one unit derived from an essential construction monomer selected from unsaturated carboxylic acids and derivatives thereof, 2) polymers containing a unit derived from styrenesulfonic acid as an essential construction monomer, 3) formalin condensates of sulfonated polycyclic aromatic compounds that may be substituted with a hydrocarbon group.

These anionic oligomers and polymers (1) to (3) according to the present invention will be described in more detail.

1) Polymers containing at least one unit derived from an essential construction monomer selected from the group consisting of unsaturated carboxylic acids and derivatives thereof.

Examples of the monomer used in production of the polymer of (1) include unsaturated monocarboxylic acids such as acrylic and methacrylic acids, unsaturated dicarboxylic acids such as maleic acid, and derivatives thereof such as alkyl esters (e.g., methyl ester) of these acids, and polyoxyethylene esters. These monomers may be used together with a copolymerizable monomer such as vinyl acetate, isobutylene, diisobutylene, and styrene as a copolymerizable component to produce the polymer.

The monomers may be polymerized conventionally. The monomer proportions and the polymerization degree are not limited.

Specific examples of the polymer of (1) include acrylic acid polymers, methacrylic acid polymers, acrylic acid-methacrylic acid copolymers, acrylic acid-polyoxyethylene methacrylate copolymers, acrylic acid-methyl acrylate copolymers, acrylic acid-vinyl acetate copolymers, acrylic acid-maleic acid copolymers, maleic acid-isobutylene copolymers, and maleic acid-styrene copolymers. These polymers and copolymers may be used alone or in combination. The polymer of (1) may be used in a form of alkaline metal salt, ammonium salt, or organoamine salt within the extent that does not impair performances of the polymer of (1).

2) Polymers containing a unit derived from styrenesulfonic acid as an essential construction monomer A styrenesulfonic acid homopolymer can be easily produced by polymerizing styrenesulfonic acid or sulfonating polystyrene. The styrenesulfonic acid polymer has a skeleton represented by the following formula. From the viewpoints of adhesion and fixation of an agrichemical to a subject including pests, agricultural products, and weeds, the polymer preferably has a molecular weight of 300 to 20000, and more preferably 300 to 10000.

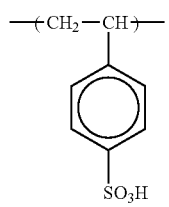

A copolymer of styrenesulfonic acid and another monomer can be easily produced by copolymerizing the monomers or sulfonating a copolymer of styrene and another monomer. Examples of the other monomer include hydrophobic monomers such as alkyl acrylates, alkyl methacrylates, vinyl alkyl ethers, vinyl acetate, ethylene, propylene, butylene, butadiene, diisobutylene, vinyl chloride, vinylidene chloride, acrylonitrile, and styrene, and hydrophilic monomers such as acrylic acid, methacrylic acid, maleic acid, fumaric acid, maleic anhydride, vinyl alcohol, acrylamide, methacrylamide, diacetone acrylamide, N-vinylpyrrolidone, 2-acrylamide-2-methylpropanesulfonic acid, and methallyl sulfonic acid. Preferred examples of the copolymer include (meth) acrylic acid-styrenesulfonic acid copolymers. As used herein, the "(meth)acrylic acid" refers to that acrylic acid and/or methacrylic acid. From the viewpoints of adhesion and fixation of an agrichemical to a subject including pests, agricultural products, and weeds, a molar ratio of (meth) acrylic acid to styrenesulfonic acid in the copolymer is preferably 1/10 to 10/1, and more preferably 1/3 to 4/1. From the same viewpoints, an average molecular weight of the copolymer is preferably 300 to 20000, and more preferably 1000 to 10000. The copolymer may have a neutralized part in the form of sodium salt, potassium salt, ammonium salt, diethanolamine salt, triethanolamine salt, monoisopropanolamine salt, diisopropanolamine salt, triisopropanolamine salt, or 2-amino-2-methylpropane-1,3-diol salt as far as performances and functions are not impaired.

3) Formalin condensates of sulfonated polycyclic aromatic compounds that may be substituted with a hydrocarbon group Specific examples of the formalin condensate include formalin condensates of petroleum sulfonic acid derivatives, lignin sulfonic acid derivatives, naphthalenesulfonic acid derivatives, xylenesulfonic acid derivatives, and alkylbenzenesulfonic acid derivatives.

The condensate of (3) can be produced by sulfonating, for example, naphthalene, an alkyl-substituted benzene, an alkyl-substituted naphthalene, anthracene, an alkyl-substituted anthracene, lignin, or a substance having an aromatic ring in a petroleum residue, and then condensing the product with formalin, according to a standard method. In this case, from the viewpoints of adhesion and fixation of an agrichemical to a subject including pests, agricultural products, and weeds, a degree of condensation is preferably not less than 2, and more preferably 3 to 30. A formalin condensate having a molecular weight of not more than 300 benefits little from the condensation and will have a problem in practical use.

As an aromatic compound to be used, a variety of aromatic compounds can be used. Preferably used are lignin, xylene, toluene, naphthalene, and alkylnaphthalenes having 1 to 6 carbon atoms. These compounds may also be used in combination.

The condensate of (3) may be used in a form of alkaline metal salt such as sodium or potassium salt, alkaline earth metal salt such as calcium salt, amine salt, or ammonium salt as far as performances and functions are not impaired.

From the viewpoints of adhesion and fixation of an agrichemical to a subject including pests, agricultural products, among polymers and oligomers of (1) to (3) described above, preferred are formalin condensates of sulfonated polycyclic aromatic compounds of (3).

The quaternary ammonium salt as described above can be easily produced, for example, by substituting a counter ion of a quaternary ammonium salt from a halogen ion for a hydroxyl ion with an ion-exchange resin, and neutralizing the quaternary ammonium salt with the oligomer or polymer having an anionic residue derived from an acid. A part of the quaternary ammonium salt may be in a form of alkaline metal salt, amine salt, or organoamine salt as far as performances and functions are not impaired.

<Component (C)>

In the present invention, the glycol ether solvent represented by the formula (C1) is used as the component (C) together with components (A) and (B):

$$R^5—O—(CH_2CH_2O)_n—H \quad (C1)$$

wherein, $R^5$ represents a linear or branched alkyl group having 1 to 6 carbon atoms or a linear or branched alkenyl group having 2 to 6 carbon atoms; and n represents 2 or 3.

It is presumed that the glycol ether solvent having the above defined structure makes the preparation of the efficacy-enhancing agent composition of the present invention easier due to a high compatibility with components (A) and (B), and provides the efficacy-enhancing agent composition with stability at a low temperature due to having a low melting point. In addition, the glycol ether solvent has a proper HLB value and thus does not impair original properties of components (A) and (B) for fixing an agrichemical.

For improving easiness in preparation, stability at low temperature, and uniform adhesion and fixation of an agrichemical, in the formula (C1), $R^5$ preferably represents a linear or branched alkyl group having 1 to 6 carbon atoms or a linear or branched alkenyl group having 2 to 6 carbon atoms, more preferably a linear or branched alkyl group having 1 to 4 carbon atoms, even more preferably a linear alkyl group having 1 to 3 carbon atoms, still even more preferably an alkyl group having 1 to 2 carbon atoms, and yet still even more preferably a methyl group. From the same viewpoints, n represents the number of 2 or 3, and more preferably 2.

For improving fixation of an agrichemical, easiness in preparation, and stability at low temperature, the component (C) has an HLB within the range of 8.0 to 15.0, and more preferably 8.5 to 14.5. As used herein, the "HLB" refers to a value equal to 10 times the ratio between an inorganic and an organic values (IOB) according to an organic concept diagram method. An inorganic and an organic values are determined, for example, as described in "Yuuki gainen zu-kiso to ouyou-(organic concept diagram method-fundamentals and applications-)", Kouda Yoshio (1985).

Examples of the component (C) include methyl carbitol, ethyl carbitol, propyl carbitol, n-butyl carbitol, diethylene glycol monoisopropyl ether, diethylene glycol monoisobutyl ether, triethylene glycol monomethyl ether, and triethylene glycol monoethyl ether. To produce the efficacy-enhancing agent composition for agricultural chemicals having good stability at low temperature and good properties for uniform adhesion and fixation of an agrichemical, the component (C) is preferably selected from methyl carbitol, ethyl carbitol, and n-butyl carbitol, and more preferably methyl carbitol. These compounds also preferably have a high flash point and can provide the efficacy-enhancing agent composition for agricultural chemicals having favorable properties in handling.

<Compositional Characteristics of the Efficacy-Enhancing Agent Composition for Agricultural Chemicals>

From the viewpoints of environmental protection and enhancement of agrichemical activity, the efficacy-enhancing agent composition for agricultural chemicals of the present invention contains the component (A) in an amount of 20 to 60% by weight, preferably 30 to 60% by weight, and more preferably 40 to 60% by weight. From the same viewpoints, the efficacy-enhancing agent composition contains the component (B) in an amount of 0.2 to 6% by weight, preferably 1 to 5.5% by weight, and more preferably 2 to 5% by weight. From the viewpoints of enhancement of agrichemical activity and stability at low temperature, the efficacy-enhancing agent composition contains the component (C) in an amount of 30 to 70% by weight, preferably 30 to 60% by weight, and more preferably 30 to 50% by weight. From the viewpoint of easiness in preparation, of the efficacy-enhancing agent composition, the total amount of components (A), (B), and (C) is preferably not less than 80% by weight, and more preferably not less than 90% by weight.

From the viewpoint of enhancement of agrichemical activity, in the efficacy-enhancing agent composition for agricultural chemicals of the present invention, a weight ratio of components (A) to (B), (A)/(B), is preferably 1/0.01 to 1/0.3, and more preferably 1/0.02 to 1/0.1.

From the viewpoints of enhancement of agrichemical activity, easiness in preparation, and stability at low temperature, a weight ratio of the component (C) to components (A) and (B), (C)/[(A)+(B)], is preferably 0.4 to 3.0, more preferably 0.5 to 2.0, even more preferably 0.6 to 1.2, still even more preferably 0.7 to 1.0, and yet still even more preferably 0.7 to 0.9.

From the viewpoint of easiness in preparation, the efficacy-enhancing agent composition for agricultural chemicals of the present invention preferably contains water in an amount of 0 to 5% by weight, more preferably 0 to 4% by weight, and even more preferably 0 to 3% by weight.

The efficacy-enhancing agent composition for agricultural chemicals of the present invention is used together with an active ingredient of an agrichemical. In practical use, the efficacy-enhancing agent composition is preferably diluted in water such that a total concentration of components (A) and (B) is 100 to 10000 ppm, and particularly 200 to 1000 ppm.

In the present invention, a surfactant other than the component (A) or (B) may be used together. Examples of the other surfactant include a nonionic surfactant and an anionic surfactant other than the component (A) or the rosin-polyoxyalkylene adduct, and a cationic surfactant and an amphoteric surfactant other than the component (B). These surfactants may be used alone or in combination.

Examples of the nonionic surfactant include polyoxyethylene alkyl ethers, polyoxyethylene alkylaryl ethers, polyoxyethylene alkylaryl ether-formaldehyde condensates, polyoxyalkylene aryl ethers, polyoxyalkylene alkyl esters, polyoxyalkylene alkyl sorbitol esters, polyoxyalkylene alkyl glycerol esters, polyoxyalkylene block copolymers, polyoxyalkylene block copolymer alkyl glycerol esters, polyoxyalkylene alkyl sulfonamides, polyoxypropylene block copolymers, polyoxyethylene oleyl ether, polyoxyalkylene alkyl phenols, alkyl glycosides, alkyl polyglycosides, polyoxyalkylene alkyl polyglycosides, and mixtures of two or more of them.

The nonionic surfactant is preferably polyethylene glycol mono- and diesters of fatty acids, and more preferably polyethylene glycol monolaurate, and polyethylene glycol monooleate.

Examples of the cationic surfactant include alkylamine-ethylene oxide adducts and alkylamine-propylene oxide adducts such as tallowamine-ethylene oxide adducts, oleylamine-ethylene oxide adducts, soyamine-ethylene oxide adducts, cocoamine-ethylene oxide adducts, synthetic alkylamine-ethylene oxide adducts, and octylamine-ethylene oxide adducts, and mixtures thereof.

Typical anionic surfactants are available in a form of aqueous liquid or solid. Examples of such surfactants include mono- and dialkylnaphthalenesulfonic acids and salts thereof, α-olefinsulfonic acid and salts thereof, alkanesulfonic acids and salts thereof, alkylsulfosuccinic acids and salts thereof, alkylsulfuric acids and salts thereof, polyoxyalkylene alkyl ether sulfuric acids and salts thereof, polyoxyalkylene alkyl aryl ether sulfuric acids and salts thereof, polyoxyalkylene styryl phenyl ether sulfuric acids and salts thereof, mono- and dialkylbenzenesulfonic acids and salts thereof, alkylnaphthalene sulfonate-formaldehyde condensates and salts thereof, alkyl diphenyl ether sulfonic acids and salt thereof, olefinic sulfonic acid and salts thereof, mono- and dialkyl phosphoric acids and salts thereof, polyoxyalkylene mono- and dialkyl phosphoric acids and salts thereof, polyoxyalkylene mono- and diphenyl ether phosphoric acids and salts thereof, polyoxyalkylene mono- and dialkyl phenyl etherphosphoric acids and salts thereof, polycarboxylic acids and salts thereof, fatty acids and salts thereof, linear and branched alkylpolyoxyalkylene ether acetic acids and salts thereof, alkenylpolyoxyalkylene ether acetic acids and salts thereof, linear and branched alkylamidepolyoxyalkylene ether acetic acids and salts thereof, stearic acid and salts thereof, oleic acid and salts thereof, N-methylfatty acid taurides, and mixtures of two or more of them (including sodium, potassium, ammonium and amine salts). For increasing performances of emulsifying and dispersing, the anionic surfactant is preferably fatty acid salts, and more preferably sodium and potassium salts of higher fatty acids such as oleic acid, and castor oil fatty acid.

Examples of the appropriate amphoteric surfactant include lauryldimethylamine oxide, Armox C/12, Monaterics, Miranols, betaines, Lonzaines, and other amine oxides, and mixtures thereof.

[Agrichemical Composition]

The agrichemical composition of the present invention contains the efficacy-enhancing agent composition for agricultural chemicals as described above and an active ingredient of an agrichemical. As used herein, the "active ingredient of an agrichemical" refers to an active component in an agrichemical.

In the agrichemical composition of the present invention, a weight ratio of the total amount of components (A) and (B) in the efficacy-enhancing agent composition for agricultural chemicals to the active ingredient of an agrichemical, [(A)+(B)]/active ingredient of an agrichemical, is preferably 0.03 to 50, more preferably 0.1 to 50, and even more preferably 0.3 to 35. However, some commercial products such as Cyharon, Scout, Nomolt, and Milbeknock are sufficiently usable at a weight ratio over 50, even about 250, depending on the dilution ratio.

The agrichemical composition of the present invention can be in any preparation form, including emulsion, liquid, wettable powder, granule, powder, and flowable concentrate. The agrichemical composition thus may contain other additive according to its preparation form, including an emulsifier, a solvent, a dispersant, and a carrier. The efficacy-enhancing agent composition for agricultural chemicals according to the present invention can be used in the above shown form of an agrichemical composition containing the efficacy-enhancing agent composition for agricultural chemicals. Alternatively the efficacy-enhancing agent composition for agricultural chemicals, separately attached, may be used when the agrichemical (containing no efficacy-enhancing agent according to the present invention) is diluted. In either of the uses, the efficacy-enhancing agent of the present invention can achieve the intended effects for enhancement.

The preparation of the agrichemical composition of the present invention may further contain a chelating agent, a pH adjusting agent, an inorganic slat, and/or a thickener according to need.

Examples of the chelating agent that can be used in the present invention include aminopolycarboxylic acid chelating agents, aromatic and aliphatic carboxylic acid chelating agents, amino acid chelating agents, ether polycarboxylic acid chelating agents, phosphonic acid chelating agents (e.g., iminodimethylphosphonic acid (IDP) and alkyldiphosphonic acid (ADPA)), dimethylglyoxime (DG), hydroxycarboxylic acid chelating agents, and polyelectrolyte (including oligomer) chelating agents. These agents may be used in a free acid form or a salt form of sodium, potassium, and ammonium.

The chelating agent is added in an amount of 0.01 to 30 moles times of the total amount of the rosin-oxyalkylene adduct and the other surfactants of the efficacy-enhancing agent composition for agricultural chemicals.

Any aminopolycarboxylic acid chelating agent can be used, including:
 a) $RNX_2$-type compounds,
 b) $NX_3$-type compounds,
 c) R—NX—$CH_2CH_2$—NX—R-type compounds,
 d) R—NX—$CH_2CH_2$—$NX_2$-type compounds, and
 e) $X_2N$—R'—$NX_2$-type compounds, wherein, X represents —$CH_2COOH$ or —$CH_2CH_2COOH$; R represents a hydrogen atom, an alkyl group, a hydroxy group, a hydroxyalkyl group, or a group representing such a known chelating compound; R' represents an alkylene group, a cycloalkylene group, or a group representing such a known chelating compound. Typical examples of this chelating agent include ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl)ethylenediaminetriacetic acid (EDTA-OH), and glycol ether diamine tetraacetic acid (GEDTA), and salts thereof.

Examples of the chelating agent that can be used in the present invention include: for aromatic and aliphatic carboxylic acid chelating agents, oxalic acid, succinic acid, pyruvic acid, anthranilic acid, and salts thereof; for amino acid chelating agents, glycine, serine, alanine, lysine, cystine, cysteine, ethionine, tyrosine, and methionine, and salts and derivatives thereof; for hydroxycarboxylic acid chelating agents, glycolic acid, malic acid, citric acid, gluconic acid, heptonic acid, acetic acid, and salts thereof; and for ether polycarboxylic acid chelating agents, compounds represented by the following formula and analogues and salts (particularly Na salt) thereof.

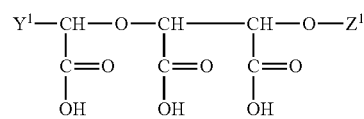

[In the formula,

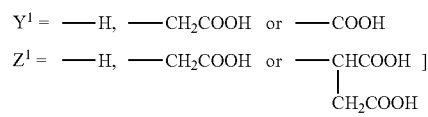

Examples of the polyelectrolyte (including oligomer) chelating agent that can be used in the present invention include acrylic acid polymers, maleic anhydride polymers, α-hydroxyacrylic acid polymers, itaconic acid polymers, and copolymers thereof, and epoxysuccinic acid polymers.

Examples of the pH adjusting agent that can be used in the present invention include citric acid, phosphoric acid (pyrophosphoric acid), gluconic acid, and salts thereof.

Examples of the inorganic salts that can be used in the present invention include inorganic mineral salts such as inorganic clay, talc, bentonite, zeolite, calcium carbonate, diatomite, and white carbon, and inorganic ammonium salts such as ammonium sulfate, ammonium nitrate, ammonium phosphate, ammonium thiocyanate, ammonium chloride, and ammonium sulfamate.

Any thickener can be used in the present invention, including natural, semisynthetic, and synthetic water-soluble thickeners. Specific examples of the thickener include: for natural viscous substances, microorganism-derived xanthan gum and Zanflow, and plant-derived pectin, gum arabic, and guar gum; for semisynthetic viscous substances, methylated, carboxyalkylated, and hydroxyalkylated celluloses and starch derivatives (including methylcellulose, carboxymethylcellulose, and hydroxymethylcellulose), and sorbitol; and for synthetic viscous substances, polyacrylates, polymaleates, polyvinylpyrrolidone, and pentaerythritol-ethylene oxide adducts.

Examples of the active ingredient of an agrichemical in the agrichemical composition of the present invention include, but not limited to, those described in "Nouyaku handobukku 2001nendoban (Agrichemical handbook 2001 edition)" (Japan Plant Protection Association). The active ingredient of an agrichemical is specifically selected from effective components of bactericides, pesticides, miticides, herbicides and plant growth regulators. The efficacy-enhancing agent composition for agricultural chemicals of the present invention has no harmful effects on various agricultural products and can be used safely.

Examples of the bactericide include sulfur-based zineb (zinc ethylenebisdithiocarbamate) and maneb (manganese ethylenebisdithiocarbamate); benzimidazole-based benomyl (methyl-1-(butylcarbamoyl)-2-benzimidazole carbamate); dicarboximide-based vinclozolin (3-(3,5-dichlorophenyl)-5-methyl-5-vinyl-1,3-oxazolidine-2,4-dione), iprodione (3-(3, 5-dichlorophenyl)-N-isopropyl-2,4-dioxoimidazolidine-1-carboxamide), and procymidone (N-(3,5-dichlorophenyl)-1, 2-dimethylcyclopropane-1,2-dicarboximide); and others such as triazine (2,4-dichloro-6-(2-chloroanilino)-1,3,5-triazine), triflumizole((E)-4-chloro-α,α,α-trifluoro-N-(1-imidazol-1-yl-2-propoxyethylidene)-o-toluidine), metalaxyl (methyl-N-(2-methoxyacetyl)-N-(2,6-xylyl)-D,L-alaninate), organocopper compounds (e.g., oxine-copper), cupric hydroxide (e.g., Kocide Bordeaux mixture), and antibiotic bactericides (streptomycins, tetracyclins, polyoxy-type bactericides, Blasticidin S, kasugamycins, and validamycins). Among these bactericides, preferred are organocopper compounds (e.g., Oxine-copper), cupric hydroxide, triflumizole ((E)-4-chloro-α,α,α-trifluoro-N-(1-imidazol-1-yl-2-propoxyethylidene)-o-toluidine), iprodione (3-(3,5-dichlorophenyl)-N-isopropyl-2,4-dioxoimidazolidine-1-carboxamide).

Examples of the pesticide include: pyrethroid pesticides such as permethrin ((3-phenoxybenzyl (1RS,3RS)-(1RS, 3RS)-3-(2,2-dichlorovinyl)-2,2-dimethylcyclopropane carboxylate); organophosphorus pesticides such as CYAP (O,O-dimethyl-O-p-cyanophenyl thiophosphate), DDVP (dimethyl 2,2-dichlorovinylphosphate); and carbamate pesticides such as Bassa (O-sec-butylphenyl methylcarbamate), MTMC (m-tolyl methylcarbamate), methomyl (S-methyl N-[(methylcarbamoyl)oxy]thioacetimide), cartap (1,3-bis(carbamoylthio)-2-(N,N-dimethylamino)propane hydrochloride). Among these pesticides, preferred are permethrin ((3-phenoxybenzyl (1RS,3RS)-(1RS,3RS)-3-(2,2-dichlorovinyl)-2,2-dimethylcyclo propane carboxylate), DDVP (dimethyl 2,2-dichlorovinylphosphate), and methomyl (S-methyl N-[(methylcarbamoyl)oxy]thioacetimide).

Examples of a natural-sourced pesticide include pyrethrin pesticide and piperonyl butoxide pesticide, derived from pyrethrum, and rotenone pesticide, derived from derris, being a leguminous plant, and nicotine pesticide (3-(1-methyl-2-pyrrolidinyl)pyridine sulfate). Examples of an insect growth regulator (IGR agent) include diflubenzuron (1-(4-chlorophenyl)-3-(2,6-difluorobenzoyl)urea).

Examples of the miticide include CPCBS (p-chlorophenyl p-chlorobenzenesulfonate), phenisobromolate (4,4'-dibromobenzilic acid isopropyl ester), tetradifon (2,4,5,4'-tetrachlorodiphenylsulfone), fenothiocarb (S-4-phenoxybutyl dimethylthiocarbamate), fenpyroximate (tert-butyl (E)-α-(1, 3-dimethyl-5-phenoxypyrazol-4-ylmethyleneaminooxy)-p-toluate), and amitraz(3-methyl-1,5-bis(2,4-xylyl)-1,3,5-triazapenta-1,4-diene). Among these miticides, preferred are phenisobromolate (4,4'-dibromobenzilic acid isopropyl ester), amitraz (3-methyl-1,5-bis(2,4-xylyl)-1,3,5-triazapenta-1,4-diene), and fenpyroximate (tert-butyl (E)-α-(1,3-dimethyl-5-phenoxypyrazol-4-ylmethyleneaminooxy)-p-toluate).

Examples of the herbicide include: acid amide herbicides such as Stam (3,4-dichloropropionanilide, DCPA); urea herbicides such as DCMU (3-(3,4-dichlorophenyl)-1,1-dimethylurea), and linuron (3-(3,4-dichlorophenyl)-1-methoxy-1-methylurea); dipyridyl herbicides such as paraquat (1,1'-dimethyl-4,4'-bipyridinium dichloride) and diquat (6,7-dihydrodipyrido[1,2-a:2',1'c]pyrazinediium dibromide); diazine herbicides such as bromacil (5-bromo-3-sec-butyl-6-methyluracil); S-triazine herbicides such as simazine (2-chloro-4,6-bis(ethylamino)-1,3,5-triazine); nitrile herbicides such as DBN (2,6-dichlorobenzonitrile); and amino acid herbicides such as glyphosate (N-(phosphonomethyl) glycine and a salt thereof). Among these herbicides, preferred are DBN (2,6-dichlorobenzonitrile), DCMU (3-(3,4-dichlorophenyl)-1,1-dimethylurea), paraquat (1,1'-dimethyl-4,4'-bipyridinium dichloride), and diquat (6,7-dihydrodipyrido[1, 2-a:2',1'c]pyrazinediium dibromide).

Examples of the plant growth regulator include indolebutyric acid, ethychlozate (ethyl 5-chloro-3-(1H)indazolylacetate), benzylaminopurine (6-(N-benzylamino)purine), forchlorfenuron (1-(2-chloro-4-pyridyl)-3-phenylurea), gibberellin, decyl alcohol, and ethephon (2-chloroethylphosphonic acid).

The agrichemical composition of the present invention can further contain one or more other plant growth regulators, fertilizers, and/or preservatives than those described above in combination.

In the present invention, for bactericidal, pesticidal, miticidal, or herbicidal purpose or purpose of control of plant growth, used is the agrichemical composition containing an active ingredient of an agrichemical and the efficacy-enhancing agent composition of the present invention in an amount of 0.03 to 50 times, preferably 0.1 to 50 times, and more preferably 0.3 to 35 times the amount of the active ingredient of an agrichemical.

The agrichemical preparation containing the efficacy-enhancing agent composition of the present invention may be composed of an individual package of the efficacy-enhancing agent composition of the present invention and an individual package of an agrichemical composition, or an individual package of components (A) and (B), an individual package of other surfactant (s) than the components (A) and (B), and an individual package of an agrichemical composition. As used herein, the "individual package of an agrichemical composition" refers to a package containing the active ingredient of an agrichemical and any optional ingredient at any ratio in the form of emulsion, a wettable powder or the like. The individual package of such an agrichemical composition differs from the agrichemical composition containing the efficacy-enhancing agent of agrichemical activity of the present invention and an active ingredient of an agrichemical. Each individual package can have any form and be adequately prepared according to an intended use and purpose.

The present invention also provides the method for increasing an agricultural product productivity, containing applying the efficacy-enhancing agent composition of the present invention and an active ingredient of an agrichemical, or the agrichemical composition (containing the efficacy-enhancing agent composition of the present invention and the active ingredient of an agrichemical) to a subject to the active ingredient of an agrichemical during agricultural product production. In other words, the present invention provides the method for cultivating an agricultural product, containing applying the agrichemical composition containing the efficacy-enhancing agent composition for agricultural chemicals containing (A) the sorbitan fatty acid ester surfactant, (B) the rosin-oxyalkylene adduct surfactant or the quaternary ammonium salt surfactant represented by the formula (B1), and (C) the glycol ether solvent represented by the formula (C1), with the content of (A) of 20 to 60% by weight, the content of (B) of 0.2 to 6% by weight and the content of (C) of 30 to 70% by weight; and an active ingredient selected from effective ingredients in bactericides, pesticides, miticides, herbicides, and plant growth regulators to a subject to the active ingredient of an agrichemical. The same preferred embodiments described above are applicable to the efficacy-enhancing agent composition in this method.

The present invention also provides the method for enhancing effects of an agrichemical, containing applying the efficacy-enhancing agent composition of the present invention and an active ingredient of an agrichemical, or the agrichemical composition (containing the efficacy-enhancing agent composition of the present invention and the active ingredient of an agrichemical) to a subject to the active ingredient of an agrichemical. In other words, the present invention provides the method for enhancing effects of an agrichemical, containing applying the agrichemical composition containing the efficacy-enhancing agent composition for agricultural chemicals containing (A) the sorbitan fatty acid ester surfactant, (B) the rosin-oxyalkylene adduct surfactant or the quaternary ammonium salt surfactant represented by the formula (B1), and (C) the glycol ether solvent represented by the formula (C1), with the content of (A) of 20 to 60% by weight, the content of (B) of 0.2 to 6% by weight and the content of (C) of 30 to 70% by weight, and an active ingredient selected from effective ingredients in bactericides, pesticides, miticides, herbicides, and plant growth regulators to a subject to the active ingredient of an agrichemical. The same preferred embodiments described above are applicable to the efficacy-enhancing agent composition in this method.

In these methods for cultivating an agricultural product and enhancing effects of an agrichemical, the efficacy-enhancing agent composition of the present invention is used together with an active ingredient of an agrichemical in practical use of an agrichemical. The subject to the active ingredient of an agrichemical in these methods includes bacteria to bactericides, pests (insects) to pesticides, mites to miticides, weeds (not falling under the category of agricultural product) to herbicides, and agricultural products (plant to be cultivated) to plant growth regulators. These methods can be applied to a single subject or multiple subjects. These methods can be performed as targeting to a subject selected from plants, pests, and bacteria, for example, by spreading the agrichemical composition onto a farmland. In this case, plants include agricultural products and/or weeds.

In the method for enhancing effects of an agrichemical, the efficacy-enhancing agent composition for agricultural chemicals of the present invention may be added to an agrichemical composition containing an active ingredient selected from effective ingredients in bactericides, pesticides, miticides, herbicides, and plant growth regulators when the agrichemical composition is applied to a subject.

In these methods of the present invention, examples of the agricultural product as the subject of the efficacy-enhancing agent composition of the present invention and an active ingredient of an agrichemical, or the agrichemical composition (containing the efficacy-enhancing agent composition of the present invention and an active ingredient of an agrichemical) include fruit vegetables such as cucumber, pumpkin, watermelon, melon, tomato, eggplant, green pepper, strawberry, okra, green bean, broad bean, pea, edamame bean, and corn; leaf vegetables such as napa cabbage, brassica vegetables, baby bok choy, cabbage, cauliflower, broccoli, Brussels sprout, onion, leek, garlic, Chinese onion, garlic chives, asparagus, lettuce, butterhead lettuce, celery, spinach, garland chrysanthemum, parsley, Japanese honewort, Japanese parsley, Japanese spikenard, myoga ginger, giant butterbur, and Japanese basil; and root vegetables such as Japanese radish, turnip, edible burdock, carrot, potato, eddoe, sweet potato, yam, ginger, lotus; and others such as rice, Triticeae agricultural products, and flowers and ornamental plants.

Examples of the weed include Bermuda grass (Cynodon dactylon), crowfootgrass (Dactyloctenium aegyptium), jungle rice (Echinochloa colona), barnyard grass (Echinochloa crus-galli), goosegrass (Eleusine indica), southern crabgrass (Digitaria ciliaris), cogongrass (Imperata cylindrica), southern cut grass (Leersia hexandra), Chinese sprangletop (Leptochloa chinensis), torpedograss (Panicum repens), Napier grass (Pennisetum purpureum), itchgrass (Rottboellia exaltata), cattail grass (Setaria pallide-fusca), smallflower umbrella sedge (Cyperus difformis), rice flatsedge (Cyperus iria), purple nutsedge (Cyperus rotundus), KUROTAMAGAYATSURI (Fuirena ciliaris), Indian jointvetch (Aeschynomene indica), tropic ageratum (Ageratum conyzoides), sessile joyweed (Alternanthera sessilis), redroot (Amaranthus retroflexus), tropical spiderwort (Commelina benghalensis), spreading dayflower (Commelina diffusas. Burm, f.), water hyacinth (Eichhornia crassipes), garden spurge (Euphorbia pilulifera), Indian heliotrope (Heliotropium indicum), Tea Bush (Hyptis suaveolens), European water clover (Marsilea crenata C. Presl), sensitive plant (Mimosa pudica), KONAGI (Monochoria vaginalis var. plantaginea), common purslane (Portulaca oleracea), coat buttons (Tridax procumbens), velvetleaf (Abutilon theophrasti), and field horsetail (Equisetum arvense).

EXAMPLES

The following Examples demonstrate the present invention. Examples are intended to illustrate the present invention, and not to limit the present invention.

Efficacy-enhancing agent compositions shown in Table 1 were prepared and evaluated as follows. Results are shown in Table 1. Some compositions of Comparative Examples were not fully evaluated, because these were rated as "B" of easiness in preparation or "D" of stability at low temperature (in Table 1, represented as "-").

(1) Easiness in Preparation

A prepared composition was immediately evaluated for its appearance at 20° C. and 60° C., and rated according to the following rating. The observation at 60° C. was performed on the assumption that the composition is subjected to that temperature in preparation.

A: A composition is homogeneous and has good fluidity at both 20° C. and 60° C.

B: A composition separates or forms a precipitation at either or both 20° C. and 60° C.

(2) Stability at Low Temperature

A prepared composition was stored for 30 days at 0° C., and then evaluated for appearance and rated according to the following 4-point scale.

A: A stored composition is homogeneous in appearance and has good fluidity, and thus can be used as is.

B: A stored composition generates small precipitations but is almost homogeneous in appearance and has good fluidity, and thus can be used as is.

C: A stored composition separates into phases, but can be shaken or agitated to become a usable state.

D: A stored composition separates, forms a precipitation, and/or coagulates, and is difficult to become a usable state by shaking or agitating.

(3) Wettability

A 1000-fold dilution of an efficacy-enhancing agent composition in distilled water was used to measure a surface tension and a contact angle according to the following methods.

surface tension: Wilhelmy method
  contact angle: 2 μL of the dilution was put on a sheet of Parafilm (American National Can Co., Parafilm M) and allowed to stand for one minute. An image of drop was taken and used to measure a contact angle.

(4) Fixing Rate of an Agrichemical

To a 50-fold dilution of a copper agrichemical (Kocide Bordeaux/bactericide) was added a 1000-fold dilution of an efficacy-enhancing agent composition. 100 μL of the dilution was applied on an acrylic plate (5 cm by 2 cm), dried, and subjected to a washing treatment with water. The washing treatment with water contained immersing the acrylic plate for 30 seconds in water in a 500 ml beaker, taking off from the water, and repeatedly moving into and out of the water ten times (one second/one time). A remaining copper ingredient on the acrylic plate was extracted with 0.1 N hydrochloric acid and measured with a simple measuring instrument RQflex. The result was used to calculate a fixing rate of an agrichemical according to the following equation. In this evaluation, for easy analysis, Kocide Bordeaux was diluted to a higher concentration (50-fold dilution) than a usual concentration, which is generally used as a 500- to 2000-fold dilution. Kocide Bordeaux used was as follows.

* Kocide Bordeaux
  Pesticide registration number: 15552
  Manufacturer: Sankyo Agro, Co. Ltd.
  Effective ingredient: cupric hydroxide 76.8% (copper 50.0%)

Fixing rate of an agrichemical(%)=(measured amount)/(theoretical initial amount of copper attached)×100

Theoretical initial amount of copper attached: calculated amount of copper attached before the washing treatment(considered as 100% fixation)=(concentration of copper agrichemical in a dilution)×(content of copper in an agrichemical)×(amount of a dilution applied)=1000 μg

TABLE 1

| | | | | Example | | | | | | | | | Comparative Example | | |
|---|---|---|---|---|---|---|---|---|---|---|---|---|---|---|---|
| | | | | 1 | 2 | 3 | 4 | 5 | 6 | 7 | 8 | 9 | 1 | 2 | 3 |
| Efficacy-enhancing agent composition for agricultural chemica | Components (% by weight) | (A) | Sorbitan monoleate | 50.0 | 50.0 | 50.0 | 50.0 | 40.0 | 50.0 | 53.0 | 53.0 | 60.0 | 71.0 | 50.0 | 50.0 |
| | | (B) | POE(18) rosin ester | 3.9 | 3.9 | 3.9 | | 3.2 | | 4.1 | 4.1 | 4.7 | 5.6 | 3.9 | 3.9 |
| | | | Quaternary ammonium salt(1) *1 | | | | 0.5 | | 0.5 | | | | | | |
| | | | Fatty acid potassium salt soap *2 | 0.92 | 0.92 | 0.92 | 1.98 | 0.76 | | 0.98 | 0.98 | 1.12 | 1.32 | 0.92 | 0.92 |
| | | (C) | Methyl carbitol | 43.3 | | | 43.0 | 54.5 | 49.0 | | | | | | |
| | | | Ethyl carbitol | | 43.3 | | | | | 39.9 | | 31.9 | | | |
| | | | n-Butyl carbitol | | | 43.3 | | | | | 39.9 | | | | |
| | | | Isobutanol | | | | | | | | | | 19.4 | 43.3 | |
| | | | Isopropanol | | | | | | | | | | | | 43.3 |
| | | | Dimethylsulfoxide | | | | | | | | | | | | |
| | | | Propylene glycol | | | | | | | | | | | | |
| | | | Dipropylene glycol | | | | | | | | | | | | |
| | | | Ethylene glycol | | | | | | | | | | | | |
| | | | 2-ethyl-1-hexanol | | | | | | | | | | | | |
| | | | Diethylene glycol dimethyl ether | | | | | | | | | | | | |
| | | | Diethylene glycol dibutyl ether | | | | | | | | | | | | |
| | | | 2-ethylhexyl carbitol | | | | | | | | | | | | |
| | | | Diethylene glycol | | | | | | | | | | | | |
| | | | Propylene glycol monomethyl ether | | | | | | | | | | | | |

TABLE 1-continued

| | | | | | | | | | | | | |
|---|---|---|---|---|---|---|---|---|---|---|---|---|
| | Methyl cellsolve | | | | | | | | | | | |
| | Other components*³ | 1.88 | 1.88 | 1.88 | 4.52 | 1.54 | 0.5 | 2.02 | 2.02 | 2.28 | 2.68 | 1.88 | 1.88 |
| | (C)/[(A) + (B)] (weight ratio) | 0.80 | 0.80 | 0.80 | 0.85 | 1.26 | 0.97 | 0.70 | 0.70 | 0.49 | 0.25 | 0.80 | 0.80 |
| Easiness in preparation | | A | A | A | A | A | A | A | A | A | A | B | B |
| Stability in low temperature | | A | A | B | A | C | B | B | B | C | D | — | — |
| Surface tension (mN/m) | | 29.9 | 29.5 | 30.8 | 29.3 | 31.5 | 30.1 | 29.7 | 30.0 | 30.8 | 31.1 | — | — |
| Contact angle (°) | | 63.7 | 65.5 | 64.6 | 63.8 | 67.3 | 64 | 63.5 | 63.0 | 64.1 | 63.5 | — | — |
| Fixing rate of an agrichemical (%) | | 77.7 | 57.7 | 66.7 | 57.0 | 58.5 | 62.0 | 61.0 | 65.1 | 62.5 | 60.7 | — | — |
| Fixing rate (%) ÷ amount of effective component (%) | | 1.44 | 1.07 | 1.23 | 1.13 | 1.35 | 1.23 | 1.15 | 1.23 | 1.04 | 0.79 | — | — |

| | | | | Example | | | | | | | | | | |
|---|---|---|---|---|---|---|---|---|---|---|---|---|---|---|
| | | | | 4 | 5 | 6 | 7 | 8 | 9 | 10 | 11 | 12 | 13 | 14 | 15 |
| Efficacy-enhancing agent composition for agricultural chemica | Components (% by weight) | (A) | Sorbitan monooleate | 50.0 | 40.0 | 50.0 | 50.0 | 71.0 | 71.0 | 50.0 | 50.0 | 50.0 | 50.0 | 50.0 | 50.0 |
| | | (B) | POE(18) rosin ester Quaternary ammonium salt(1) *¹ | 3.9 | 3.2 | 3.9 | 3.9 | 5.6 | 5.6 | 3.9 | 3.9 | 3.9 | 3.9 | 3.9 | 3.9 |
| | | | Fatty acid potassium salt soap *² | 0.92 | 0.76 | 0.92 | 0.92 | 1.32 | 1.32 | 0.92 | 0.92 | 0.92 | 0.92 | 0.92 | 0.92 |
| | | (C) | Methyl carbitol | | | | | | | | | | | | |
| | | | Ethyl carbitol | | | | | | | | | | | | |
| | | | n-Butyl carbitol | | | | | | | | | | | | |
| | | | Isobutanol | | | | | | | | | | | | |
| | | | Isopropanol | | | | | | | | | | | | |
| | | | Dimethyl-sulfoxide | 43.3 | 54.5 | | | | | | | | | | |
| | | | Propylene glycol | | | 43.3 | | | | | | | | | |
| | | | Dipropylene glycol | | | | 43.3 | | | | | | | | |
| | | | Ethylene glycol | | | | | 19.4 | | | | | | | |
| | | | 2-ethyl-1-hexanol | | | | | | 19.4 | | | | | | |
| | | | Diethylene glycol dimethyl ether | | | | | | | 43.3 | | | | | |
| | | | Diethylene glycol dibutyl ether | | | | | | | | 43.3 | | | | |
| | | | 2-ethylhexyl carbitol | | | | | | | | | 43.3 | | | |
| | | | Diethylene glycol | | | | | | | | | | 43.3 | | |
| | | | Propylene glycol monomethyl ether | | | | | | | | | | | 43.3 | |
| | | | Methyl cellsolve | | | | | | | | | | | | 43.3 |
| | | | Other components *³ | 1.88 | 1.54 | 1.88 | 1.88 | 2.68 | 2.68 | 1.88 | 1.88 | 1.88 | 1.88 | 1.88 | 1.88 |
| | | | (C)/[(A) + (B)] (weight ratio) | 0.80 | 1.26 | 0.80 | 0.80 | 0.25 | 0.25 | 0.80 | 0.80 | 0.80 | 0.80 | 0.80 | 0.80 |
| Easiness in preparation | | | | A | B | A | A | B | B | B | B | B | B | A | A |
| Stability in low temperature | | | | A | — | D | D | — | — | — | — | — | — | D | D |
| Surface tension (mN/m) | | | | 28.4 | — | — | 31.3 | — | — | — | — | — | — | — | — |
| Contact angle (°) | | | | 63.9 | — | — | 64.6 | — | — | — | — | — | — | — | — |
| Fixing rate of an agrichemical (%) | | | | 30.3 | — | — | — | — | — | — | — | — | — | — | — |
| Fixing rate (%) ÷ amount of effective component (%) | | | | 0.56 | — | — | — | — | — | — | — | — | — | — | — |

In Table 1, POE is an abbreviated expression of polyoxyethylene, and the number in parenthesis represents the average number of moles of added polyoxyethylene.

*1 Quaternary ammonium salt (1): polynaphthylmethanesulfonic acid dialkyldimethylammonium salt [the following compound corresponding to the formula (B1)]

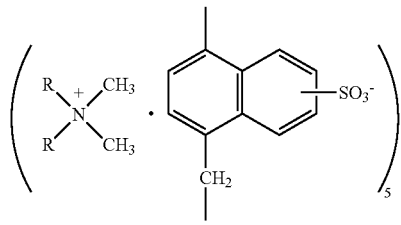

Examples 1 to 9 also exhibited equal or higher surface tension and contact angle than that of Comparative Example 1. Particularly for the fixing rate of an agrichemical, on the basis of a ratio of the fixing rate to an amount of an effective component (fixing rate/amount of an effective component), Examples 1 to 9 exhibited largely increased values than that of Comparative Example 1, showing significantly increased ability of an agrichemical to fix per effective component.

Table 2 shows physical properties of solvents used in Examples and Comparative Examples. A flash point was a measured value (with a Cleveland open cup flashpoint tester or a value described in "15509 no Kagaku Seihin (15509 chemical products)" (2009, Jan., 27, Chemical Daily Co., Ltd.). Among solvents used in Comparative Examples, for those having a structure corresponding to the formula (C1), meanings of items in the formula (C1) were shown for convenience.

TABLE 2

| | Name of compound | Structure | Structure in the formula(C1) | | | | Flash point (° C.) |
| | | | n | The number of carbon atoms of R | Molecular weight | HLB | |
|---|---|---|---|---|---|---|---|
| Used in Examples | Methyl carbitol | $CH_3$—O—$(CH_2CH_2O)_2$—H | 2 | 1 | 120 | 14.0 | 105 |
| | Ethyl carbitol | $C_2H_5$—O—$(CH_2CH_2O)_2$—H | 2 | 2 | 134 | 11.7 | 102 |
| | n-Butyl carbitol | $C_4H_9$—O—$(CH_2CH_2O)_2$—H | 2 | 4 | 162 | 8.8 | 120 |
| Used in Comparative examples | Isobutanol | $(CH_3)_2CHCH_2OH$ | — | — | 74 | 14.3 | 28 |
| | Isopropanol | $(CH_3)_2CHOH$ | — | — | 60 | 20.0 | 12 |
| | Dimethylsulfoxide | $(CH_3)_2SO$ | — | — | 78 | 17.5 | 95 |
| | Propylene glycol | HO—$(CH_2CH(CH_3)O)$—H | — | — | 76 | 33.3 | 99 |
| | Dipropylene glycol | $(CH_3CH(OH)CH_2)_2O$ | — | — | 134 | 18.3 | 138 |
| | Ethylene glycol | HO—$(CH_2CH_2O)$—H | 1 | — | 62 | 50.0 | 120 |
| | 2-ethyl-1-hexanol | $C_4H_9CH(C_2H_5)CH_2$—OH | — | — | 130 | 6.3 | 78 |
| | Diethylene glycol dimethyl ether | $CH_3$—O—$(CH_2CH_2O)_2$—$CH_3$ | 2 | — | 134 | 5.0 | 56 |
| | Diethyleneglycol dibutyl ether | $C_4H_9$—O—$(CH_2CH_2O)_2$—$C_4H_9$ | 2 | — | 218 | 2.5 | 122 |
| | Diethylene glycol mono2-ethylhexyl ether | $C_4H_9CH(C_2H_5)CH_2$—O—$(CH_2CH_2O)_2$—H | 2 | 8 | 218 | 5.8 | 151 |
| | Diethylene glycol | H—O—$(CH_2CH_2O)_2$—H | 2 | 0 | 106 | 27.5 | 138 |
| | Propylene glycol monomethyl ether | $CH_3$—O—$(CH_2CH(CH_3)O)$—H | — | — | 90 | 15.0 | 32 |
| | Methyl cellosolve | $CH_3$—O—$(CH_2CH_2O)$—H | 1 | 1 | 76 | 20.0 | 39 |

*2 Fatty acid potassium salt soap: a fatty acid preparation containing castor oil fatty acid and a small amount of water was used

*3 Other ingredient: water (moisture derived from the fatty acid potassium salt soap preparation)

Efficacy-enhancing agent compositions of Examples were easily prepared and had good stability at low temperature, proper surface tension and contact angle, and a good fixing rate of an agrichemical. In contrast, efficacy-enhancing agent compositions of Comparative Examples did not fully satisfy the evaluation items simultaneously. In the evaluations, the surface tension and the contact angle are indicators of properties to wet spread (uniform adhesion) on plants, and the smaller values thereof are the better. The fixing rate of an agrichemical shows a degree of remaining of an agrichemical attached on a plant after rainfall or the like, and the larger value is the better. In cases of adding no efficacy-enhancing agent composition for agricultural chemicals, the fixing rate is generally about 5% under test conditions of the present invention. As shown in Table 1, Examples 1 to 9 exhibited a fixing rate of an agrichemical equal to or higher than that of Comparative Example 1, with less amounts of effective components [components (A) and (B)] in Examples 1 to 9.

The invention claimed is:

1. An efficacy-enhancing agent composition for agricultural chemicals, comprising (A) a sorbitan fatty acid ester surfactant, (B) a rosin-oxyalkylene adduct surfactant or a quaternary ammonium salt surfactant represented by the formula (B1), and (C) a glycol ether solvent represented by the formula (C1), wherein the content of (A) is 20 to 60% by weight, the content of (B) is 0.2 to 6% by weight and the content of (C) is 30 to 70% by weight:

wherein at least one of $R^1$, $R^2$ and $R^3$ is a linear or branched alkyl or alkenyl group, having 8 to 30 carbon atoms, the other is one of —$CH_3$, —$CH_2CH_3$,

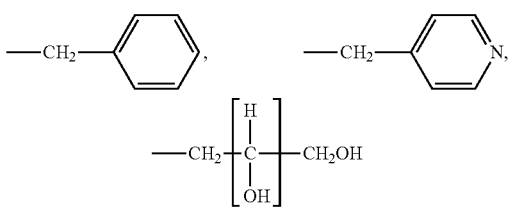

wherein n=1 to 5,
or combination thereof;
$R^4$ represents —$CH_3$ or —$CH_2CH_3$; and
a counter ion $X^-$ represents one, two or more anionic groups derived from an anionic oligomer or polymer, having an average molecular weight of 300 to 20000, selected from the group consisting of the followings 1) to 3),
1) polymers comprising one, two or more units derived from an essential construction monomer selected from the group consisting of unsaturated carboxylic acids and derivatives thereof,
2) polymers comprising styrenesulfonic acid as an essential construction monomer, and
3) formalin condensates of sulfonated polycyclic aromatic compounds that may be substituted with a hydrocarbon group,

   (C1)

wherein, $R^5$ represents a linear or branched alkyl group having 1 to 6 carbon atoms or a linear or branched alkenyl group having 2 to 6 carbon atoms; and n represents 2 or 3, and
wherein a weight ratio of the component (C) to components (A) and (B), (C)/[(A)+(B)], is 0.6 to 1.2.

2. The efficacy-enhancing agent composition for agricultural chemicals according to claim 1, further comprising at least one surfactant other than the components (A) and (B).

3. The efficacy-enhancing agent composition for agricultural chemicals according claim 1, wherein a water content of the composition is 0 to 5% by weight.

4. The efficacy-enhancing agent composition for agricultural chemicals according to claim 1, wherein R5 in the formula (C1) is a linear or branched alkyl group having 1 to 3 carbon atoms.

5. The efficacy-enhancing agent composition for agricultural chemicals according to claim 1, wherein (A) the sorbitan fatty acid ester surfactant includes a sorbitan fatty acid ester.

6. The efficacy-enhancing agent composition for agricultural chemicals according to claim 1, wherein the weight ratio of component (A) to component (B) is 1/0.01 to 1/0.3.

7. An agrichemical composition, comprising the efficacy-enhancing agent composition for agricultural chemicals according to claim 1 and an active ingredient selected from the group consisting of effective ingredients in bactericides, pesticides, miticides, herbicides, and plant growth regulators, wherein a weight ratio of the total of (A) and (B) in the efficacy-enhancing agent composition to the active ingredient of an agrichemical, [(A)+(B)]/active ingredient of an agrichemical, is 0.03 to 50.

8. An agrichemical preparation, comprising an individual package of the efficacy-enhancing agent composition for agricultural chemicals according to claim 1 and an individual package of an agrichemical composition comprising an active ingredient selected from the group consisting of effective ingredients in bactericides, pesticides, miticides, herbicides, and plant growth regulators.

9. A method for cultivating an agricultural product, comprising applying an agrichemical composition comprising the efficacy-enhancing agent composition for agricultural chemicals according claim 1 and an active ingredient selected from the group consisting of effective ingredients in bactericides, pesticides, miticides, herbicides, and plant growth regulators to a subject.

10. A method for enhancing an agrichemical, comprising applying an agrichemical composition comprising the efficacy-enhancing agent composition for agricultural chemicals according to claim 1 and an active ingredient selected from the group consisting of effective ingredients in bactericides, pesticides, miticides, herbicides, and plant growth regulators to a subject.

* * * * *